(12) United States Patent
Kim

(10) Patent No.: US 10,234,398 B2
(45) Date of Patent: Mar. 19, 2019

(54) DEFORMATION VERIFICATION SYSTEM AND METHOD OF VEHICLE BODY

(71) Applicants: Hyundai Motor Company, Seoul (KR); Kia Motors Corporation, Seoul (KR)

(72) Inventor: Kyoung Hye Kim, Suwon-si (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 0 days.

(21) Appl. No.: 15/813,694

(22) Filed: Nov. 15, 2017

(65) Prior Publication Data
US 2019/0017939 A1    Jan. 17, 2019

(30) Foreign Application Priority Data

Jul. 11, 2017 (KR) ........................ 10-2017-0087967

(51) Int. Cl.
| | | |
|---|---|---|
| *G01N 21/00* | (2006.01) | |
| *G01N 21/88* | (2006.01) | |
| *G01B 11/16* | (2006.01) | |
| *B62D 65/18* | (2006.01) | |
| *B05D 1/24* | (2006.01) | |
| *F26B 15/14* | (2006.01) | |
| *B05C 9/14* | (2006.01) | |
| *G05B 19/418* | (2006.01) | |
| *C25D 17/02* | (2006.01) | |
| *C25D 21/04* | (2006.01) | |

(52) U.S. Cl.
CPC .......... *G01N 21/8806* (2013.01); *B05C 9/14* (2013.01); *B05D 1/24* (2013.01); *B62D 65/18* (2013.01); *F26B 15/14* (2013.01); *G01B 11/16* (2013.01); *C25D 17/02* (2013.01); *C25D 21/04* (2013.01); *G05B 19/41805* (2013.01)

(58) Field of Classification Search
CPC ............... G01N 21/9501; G01N 21/94; G01N 21/8806; G01N 21/956; G01N 21/95607
USPC ...................................... 356/237.2
See application file for complete search history.

(56) References Cited

U.S. PATENT DOCUMENTS

2002/0148738 A1* 10/2002 Boyd ..................... G01N 33/32
                                                            205/782
2012/0097099 A1*  4/2012 Roeckle ............. B65G 49/0459
                                                            118/423

FOREIGN PATENT DOCUMENTS

| JP | 3358513 B2 | 12/2002 |
|---|---|---|
| JP | 5774940 B2 | 9/2015 |
| KR | 1020090016339 A | 2/2009 |
| KR | 1020090055220 A | 6/2009 |
| KR | 101402983 B1 | 6/2014 |

\* cited by examiner

*Primary Examiner* — Md M Rahman
(74) *Attorney, Agent, or Firm* — Slater Matsil, LLP

(57) ABSTRACT

A deformation verification system of a vehicle body includes a dip tank in which fluid is contained. The dip tank has a transparent window from the outside to see the inside. A moving device is configured to lower the vehicle body into the fluid, to move the vehicle body in the fluid and to raise the vehicle body. A camera is installed to detect the form of the vehicle body through the transparent window.

18 Claims, 5 Drawing Sheets

DEFORMATION VERIFICATION SYSTEM AND METHOD OF VEHICLE BODY

CROSS-REFERENCE TO RELATED APPLICATIONS

This application claims the benefit of Korean Patent Application No. 10-2017-0087967, filed in the Korean Intellectual Property Office on Jul. 11, 2017, which application is hereby incorporated herein by reference.

TECHNICAL FIELD

The present invention relates to a deformation verification system and method of a vehicle body.

BACKGROUND

In a painting process of a vehicle body, a vehicle body passes through a number of pretreatment and electrodeposition dipping process in order to remove the contaminants and improve the rust prevention.

During these processes, buoyancy and fluid pressure are applied to the vehicle body, causing the vehicle body to float or deform in the vehicle body, thereby affecting the level difference as the appearance quality of the vehicle.

However, the pretreatment and electrodeposition process is a process that cannot be confirmed internally, and it is impossible to predict the effect of the paint on the body and the behavior of the body in the paint.

At each stage of new car development, the solution has been derived by testing at the mass production plant.

Particularly, during mass production, there is a concern that the vehicle body may come off because the new vehicle and the mounting part of the transportation device do not fit, and it is difficult to secure quality until mass production due to limitation on schedule, and so on.

That is, in the conventional art, since the deep tank is a structure that is close and sealed, it is impossible to confirm the internal phenomenon when verifying the new vehicle at the mass production plant. Also, since the vehicle body must be inserted and tested during production, there are restrictions on the number of tests, the schedule of vehicle body input, and the number of vehicle body input, so that it is difficult to secure quality through the reinforcement by trial and error.

As described above, if quality assurance is delayed, man-hours depending on the design change after the mass production mold is started can be added to the moving part.

Further, in the case of a new vehicle to be introduced along with the construction of a new factory, since pre-verification thereof is not possible, it is being replaced by inspection at other factories with similar conditions so that it is difficult to drive an accurate verification result and it may reduce safety and operating rate because the vehicle body is put in a state where the transportation equipment is not fitted.

Furthermore, when verifying the deformation of the vehicle body after electrodeposition, the vehicle body is transferred to the test area and measured after the moving part is separated so that it is difficult to verify accurately due to the separation and mounting of the moving part, and it is impossible to pre-verify the vehicle because the test area is made at the stage of new vehicle production.

FIG. 5 is a cross-sectional view showing a dip tank of an electrodeposition painting related to the present invention.

Referring to FIG. 5, a dip tank 150 is opened at the upper portion thereof and paint or pretreatment solution is filled therein.

The dip tank is provided with an input portion for inputting a vehicle body 140 at one side and an output portion at the other side. A nozzle or valves for filling and circulating the paint or the pretreatment solution may be provided.

For the contents of the main conventional art, reference can be made to the following prior art document patents: Korea Application Patent No.: 10-2007-0122028 and Korea Application Patent No.: 10-2007-0080893.

The above information disclosed in this Background section is only for enhancement of understanding of the background of the invention and therefore it may contain information that does not form the prior art that is already known in this country to a person of ordinary skill in the art.

SUMMARY

Embodiments of the present invention relate to a deformation verification system and method of a vehicle body capable of minimizing the deformation of a vehicle body during a painting process by detecting the deformation of the vehicle body due to the lifting force of the vehicle body or the paint pressure generated in an electrodeposition process.

Embodiments have advantages of reproducing the painting conditions without lowering safety and operating rate, and economically verifying the lifting force and post-deformation of the vehicle body in advance.

A deformation verification system of a vehicle body according to an exemplary embodiment of the present invention may include a dip tank in which fluid is contained and having a transparent window from the outside to see the inside. A moving device lowering the vehicle body into the fluid can move the vehicle body in the fluid and raise the vehicle body. A camera is installed to detect the form of the vehicle body through the transparent window.

The camera may sense a first form of the vehicle body before the vehicle body is immersed in the fluid in the dip tank, detect the intermediate form of the vehicle body in the state that the vehicle body is moving in the fluid of the dip tank, and detect a second form of the vehicle body after the vehicle body is removed from the fluid in the dip tank.

A control/calculation unit calculates the form variation of the vehicle body according to the first form, the intermediate form and the second form.

The control/calculation unit may generate a retest signal depending on the form variation of the vehicle body.

The control/calculation unit may generate the retest signal if the form variation is determined to be greater than a predetermined value.

The control/calculation unit may receive predetermined process conditions, and may move the vehicle body to a predetermined speed along a predetermined route according to the process conditions.

The moving device may include a mounting portion on which the vehicle body is mounted, a horizontal transfer portion for moving the mounting portion in a horizontal direction, an up and down transfer portion for moving the mounting portion in the up and down direction, and a rotation portion for rotating the mounting portion about a rotation center.

The horizontal transfer portion may include a horizontally moving member that moves along a rail, and the up and down transfer portion may include an up and down moving member that moves up and down in the horizontal moving member. The rotation portion may be disposed on an end portion of the up and down moving member in order to rotate the mounting portion.

The fluid may be water, electrodeposition paint, or pre-processing liquid, and may have a certain transparency.

In the fluid space of the dip tank, a circulation device may be installed to control the flow of the fluid.

The moving device may include a conveyor and may further include a lighting device installed inside or outside of the dip tank to illuminate the area where the camera is to be photographed.

A deformation verification method according to an exemplary embodiment of the present invention may include putting a vehicle body into the fluid contained in a dip tank at which a transparent window visible from the outside to the inside is installed. The vehicle body is moved and the form of the vehicle body moving inside the dip tank is shot through the transparent window.

The step of exhausting the vehicle body in the fluid to the outside may be further included.

The step of shooting may detect a first form of the vehicle body before the vehicle body is immersed in the fluid of the dip tank, detect an intermediate form of the vehicle body with the vehicle body moving into the fluid of the dip tank and detect a second form of the vehicle body after the vehicle body is removed from the fluid in the dip tank.

After the step of shooting, a step of calculating a form variation of the vehicle body according to the first form, the intermediate form and the second form may further included.

A retest signal depending on the form variation of the vehicle body may be generated in the calculating step.

In the calculating step, if it is determined that the form variation is above the predetermined value, the retest signal may be generated.

The step of receiving predetermined process conditions may be included. The vehicle body may be moved at a set speed according to the set route depending on the process conditions.

In the moving step, the vehicle body may be moved horizontally, moved up and down, and rotated.

The fluid may be circulated in the dip tank in a predetermined direction and a predetermined speed.

According to the present invention, it is possible to effectively verify the levitation force or deformation factors applied to the vehicle body during the painting pretreatment or electrodeposition process.

Furthermore, it is possible to improve the stability at the painting factory and reproduce the paint conditions without deteriorating the utilization rate in the actual vehicle painting factory, and it is possible to effectively verify the lifting force and deformation of the vehicle body in advance.

DETAILED DESCRIPTION OF ILLUSTRATIVE EMBODIMENTS

Figure 1:
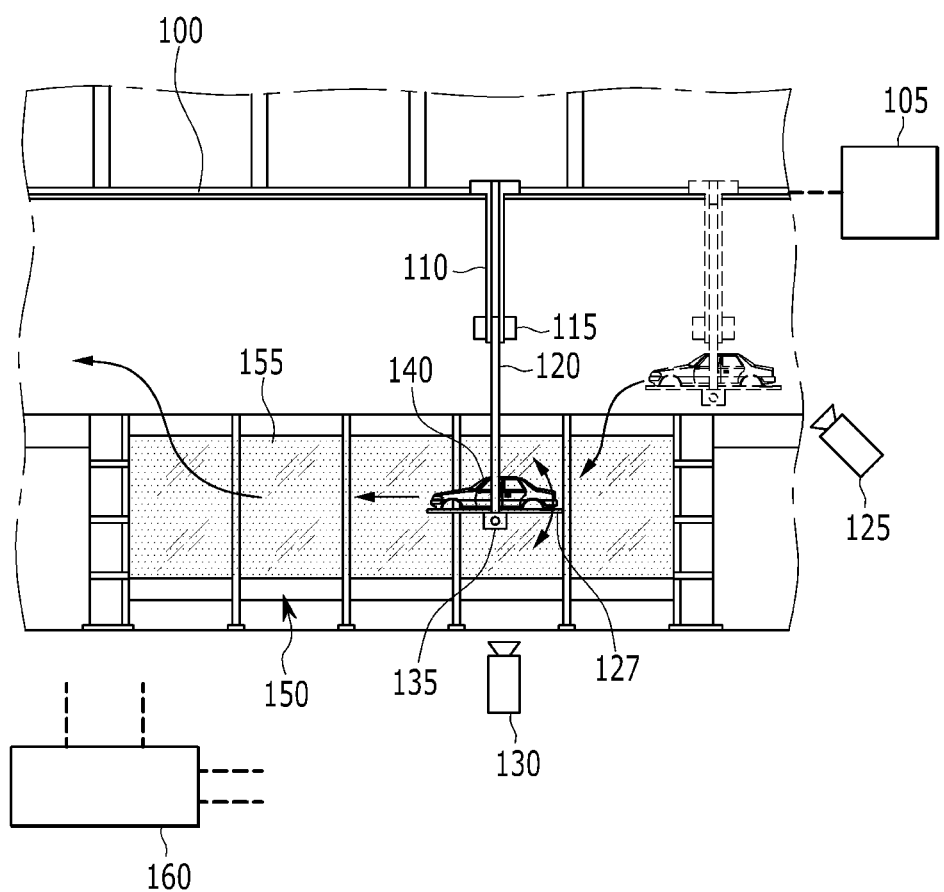
FIG. 1 is a side view of the deformation verification system of a vehicle body according to an exemplary embodiment of the present invention.

Hereinafter, an exemplary embodiment of the present invention will be described in detail with reference to accompanying drawings.

However, since the size and thickness of each element shown in the drawing are arbitrarily shown for convenience of explanation, the present invention is not necessarily limited to that shown in the drawing, and the thickness is enlarged to clearly represent the various parts and regions.

In order to clearly illustrate an exemplary embodiment of the present invention, the parts not related to the description are omitted, and the same reference element is assigned to the same or similar constituent elements throughout the specification.

In the following description, to distinguish the names of the elements into first, second, and the like is to distinguish these because the names of the elements are the same, and it is not necessarily limited to the order.

In an exemplary embodiment of the present invention, a pretreatment and an electroplating dipping process consisting of 9 to 10 cycles are carried out to remove contaminants from the vehicle body and to improve rust resistance in a painting process.

During the vehicle body performs above process, the vehicle body may be floated or deformed due to the float force and fluid pressure, which may affect the gap and step of the vehicle body.

However, the pre-treatment and electrodeposition dipping processes are not identifiable internally, and the effects of fluid on the vehicle body and methods for predicting the form variation of the vehicle body are researched.

FIG. 1 is a side view of the deformation verification system of a vehicle body according to an exemplary embodiment of the present invention.

Referring to FIG. 1, a deformation verification system of a vehicle body may include a 3D camera 125, a mounting portion 127, a 3D high-speed camera 130, a rotation portion 135, a vehicle body 140, a dip tank 150, a transparent window 155, a conveyor 100, a horizontal moving member 110, an up and down moving member 120, an up and down transfer portion 115, a horizontal transfer portion 105 and a control/calculation unit 160.

The dip tank 150 is open at the top and contains fluid to test the electrodeposition painting process therein, and the transparent window 155 is formed on one side of the dip tank 150.

In an exemplary embodiment of the present invention, the operator, or experimenter, may look into the dip tank 150 through the transparent window 155.

The 3D high-speed camera 130 may capture the form of the vehicle body 140, which is immobilized to the fluid of the dip tank iso, and the 3D camera 125 may capture the form of the vehicle body 140 before being immersed in the fluid in the dip tank iso.

The control/calculation unit 160 may determine if the conditions, including the speed at which the vehicle body 140 moves into the fluid, are satisfied or not by using the form of the vehicle body 140 taken at the 3D high-speed camera 130 and the 3D camera 125.

On the upper side of the bottom tank 150, a conveyor 100 or a rail may formed in a horizontal direction, and the conveyor may include a rail or be replaced by a rail.

The horizontal transfer portion 105 can move the horizontal moving member no in a predetermined direction using the conveyor or rail, the up and down moving member 120 may be disposed on the horizontal moving member 110, the up and down transfer portion 115 can move the up and down moving member 120 up and down on the horizontal moving member 110.

The mounting portion 127 may be disposed on the lower end of the up and down moving member 120 and the vehicle body 140 may be disposed on the mounting portion 127.

The rotation portion 135 may rotate the mounting portion 127.

The control/calculation unit 160 controls the horizontal transfer portion 105, the up and down transfer portion 115, and the rotation portion 135, respectively, so that the vehicle body 140 mounted on the mounting portion 127 moves horizontally from one side of the upper portion of the dip tank 150 and descends into the fluid contained in the dip tank 150.

With the vehicle body immerged in the fluid in the dip tank 150, the vehicle body 140 rotates, moves from one side to the other side, and rises from the other side of the dip tank 150 to the upper side of the fluid.

During the vehicle body 140 moves in the fluid, the vehicle body 140 is subjected to lifting force and fluid pressure so that the vehicle body 140 may be deformed.

In an exemplary embodiment of the present invention, the route, speed and rotation speed of the vehicle body 140 may be changed according to the process condition. As the vehicle body 140 moves through the fluid, the route, speed, and rotation speed may vary depending on the deformation amount of the vehicle body 140.

In addition, the fluid contained in the dip tank 150 may be an electrodeposition painting, may be transparent, and may be pretreatment liquid.

Also, inside the dip tank 150, a circulation device 200 may be constructed. The circulation device 200 may circulate the fluid in a predetermined direction, which may be referred to the prior art.

In an exemplary embodiment of the present invention, the control/calculation unit 160 may be implemented as a least one microprocessor operating according to a predetermined program, and the predetermined program may include a series of instructions for performing the method according to an exemplary embodiment of the present invention described below.

Also, in an exemplary embodiment of the present invention, a lighting device (not shown) may be provided to effectively capture the interior of the dip tank, and the lighting device may be installed either inside or outside the dip tank, can be selectively installed at predetermined locations.

The device that moves the vehicle body in the horizontal direction may have a conveyor structure, and the vehicle body may move in the horizontal direction according to the operation of the conveyor.

Figure 2:
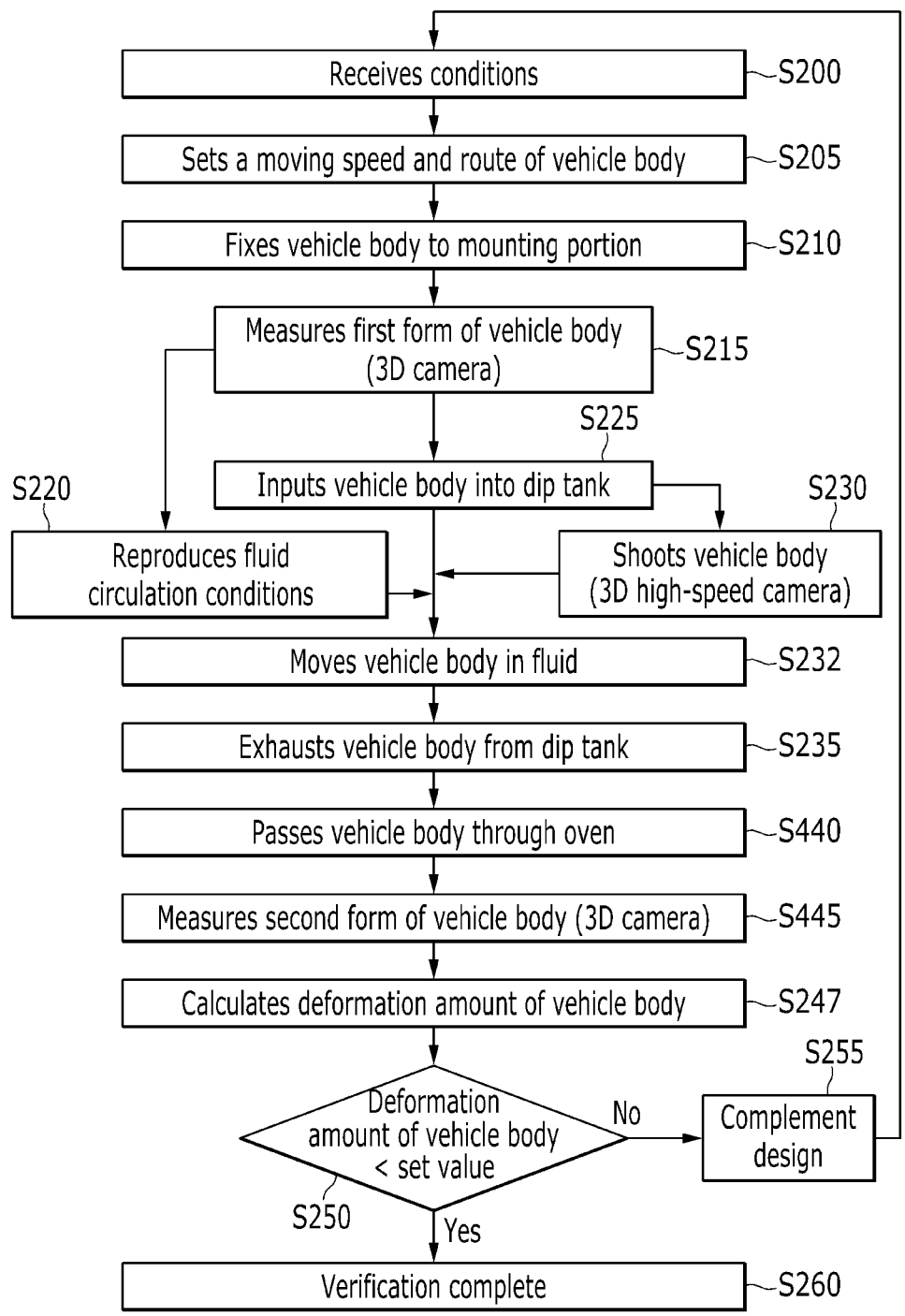
FIG. 2 is a flowchart showing a deformation verification method of the vehicle body passing the dip tank according to an exemplary embodiment of the present invention.

FIG. 2 is a flowchart showing a deformation verification method of the vehicle body passing the dip tank according to an exemplary embodiment of the present invention.

Referring to FIG. 2, process conditions are received at the step S200.

At the step S205, the control/calculation unit 160 sets the moving speed, traveling route and rotation speed of the vehicle body 140 according to the process conditions.

At the step S210, a worker or a robot mounts and fixes the predetermined vehicle body 140 in the mounting portion 127 in advance.

At the step S215, the 3D camera 125 takes the form before the vehicle body 140 is immersed in the fluid, and the conditioning condition of the fluid is reproduced in the step S220.

Then, at the step S225, the vehicle body 140 is immersed in the fluid of the dip tank 150, which may be referred to as an input step.

At the step S220, the circulating condition of the fluid (or paint) in the dip tank is reproduced.

This may be accomplished by a spray nozzle (not shown) that is immersed in the fluid and ejects the fluid in a predetermined direction.

At the step S230, the 3D high-speed camera 130 continuously captures the form of the vehicle body 140 contained in the fluid of the dip tank 150 through the transparent window 155, which may be referred to as the imaging step.

Further, the step S232 is a moving step in which the vehicle body is moved in a state of being contained in the fluid of the dip tank, and the form of the vehicle body is captured by the camera with the fluid circulation condition being implemented.

At the step S235, the transfer device 210 exhausts the vehicle body 140 out of the dip tank 150. At the step S240, the vehicle is put into the oven (not shown) to cure the sealer applied between the inner and outer plates in the hood of the vehicle body. The step S440 may be deleted.

At the step S245, the 3D camera 125 is either ejected from the dip tank 150 or taken in the form of the vehicle body 140 exhausted from the oven.

At the step S247, the control/calculation unit 160 calculates the amount of deformation of the vehicle body 140 using the front and rear forms of the vehicle body 140 photographed with the 3D camera 125 or the 3D high-speed camera 130. At the step S250, if it is determined that the deformation amount of the vehicle body 140 is less than (or below) the predetermined value, the verification is completed in the step S260.

At the step S250, if it is determined that the deformation amount of the vehicle body 140 is equal to or greater than the predetermined value, the operator may modify the design or reinforce the stiffness for the retest at the step S255.

In addition, it may automatically generate a signal for retesting and inform the operator of the retest via a display device or sound.

Figure 3:
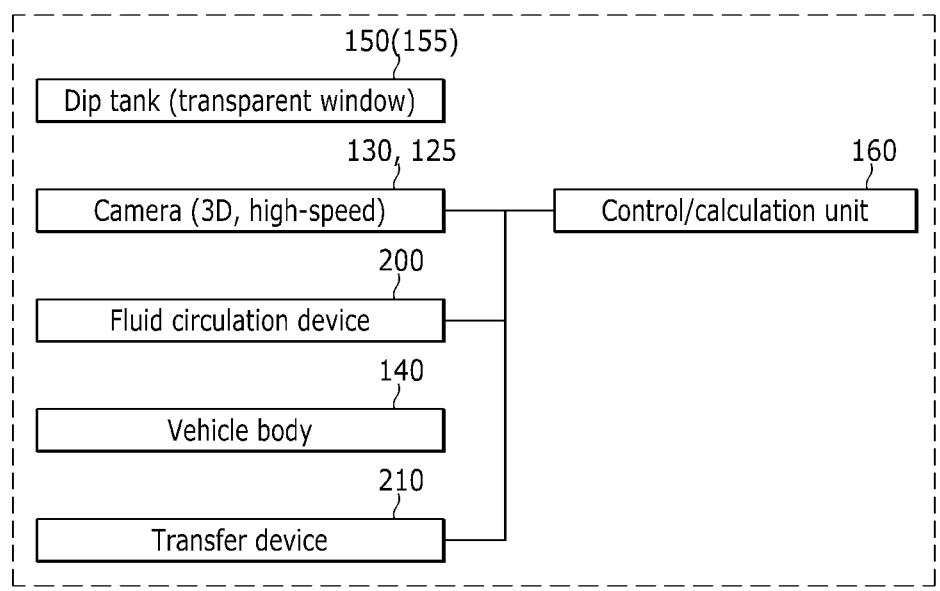
FIG. 3 is a block diagram of the deformation verification system of the vehicle body according to an exemplary embodiment of the present invention.

FIG. 3 is a block diagram of the deformation verification system of the vehicle body according to an exemplary embodiment of the present invention.

Referring to FIG. 3, deformation verification system of a vehicle body may include a dip tank 150 including a transparent window 155, cameras 130 and 125, a circulation device 200, a vehicle body 140, a transfer device 210 and a control/calculation unit 160.

The circulation device 200 may include a nozzle disposed inside the bottom tank 150 and control the flow direction and flow speed of the fluid filled inside the dip tank 150.

The cameras 130 and 125 may include all devices capable of capturing the 3D form of the vehicle body 140. In an exemplary embodiment of the present invention, the cameras 130 and 125 may include a 3D camera 125 and a 3D high-speed camera 130, or one camera.

The vehicle body 140 according to an exemplary embodiment of the present invention may be fixed on the mounting portion 127. The mounting portion 127 may accommodate a variety of vehicle bodies.

Figure 4:
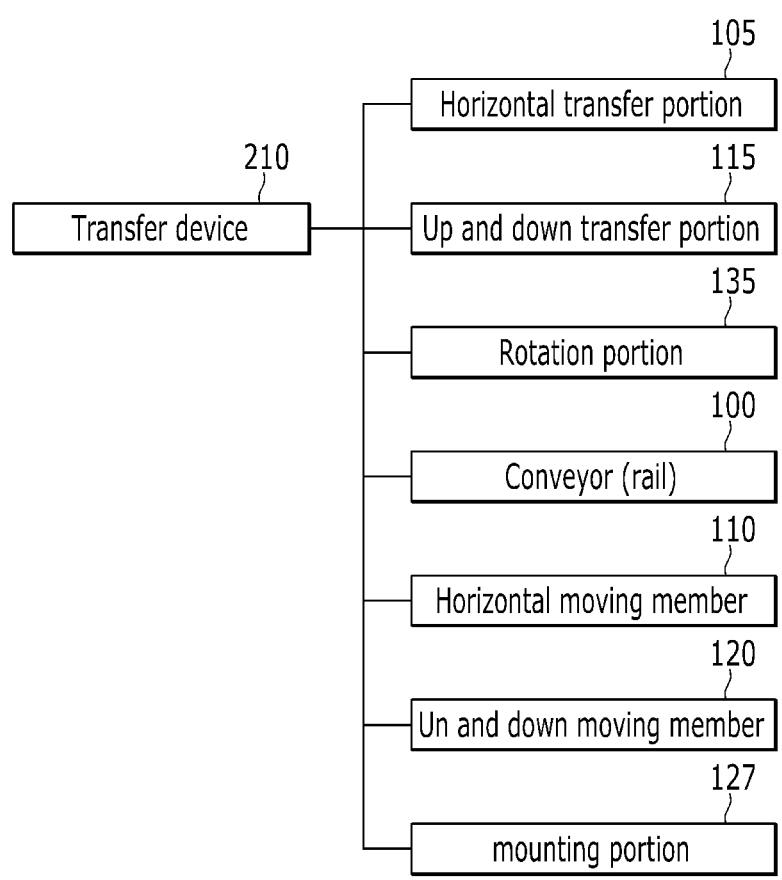
FIG. 4 is a schematic diagram showing the transfer device according to an exemplary embodiment of the present invention.
Figure 5:
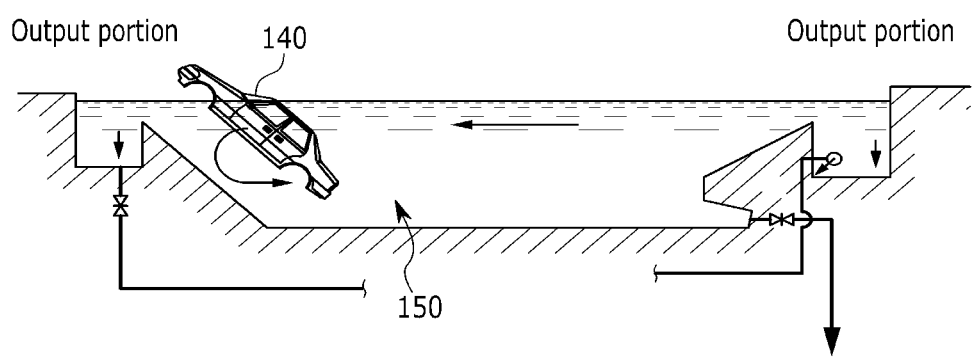
FIG. 5 is a cross-sectional view showing a dip tank of electrodeposition painting associated with the present invention.

FIG. 4 is a schematic diagram showing the transfer device according to an exemplary embodiment of the present invention.

Referring to FIG. 4, the transfer device 210 may include a conveyor 100, a horizontal transfer portion 105, an upper transfer portion 115, a rotation portion 135, a horizontal moving member 110, an up and down moving member 120, and a mounting portion 127.

The conveyor 100 may be composed of a rail.

The horizontal transfer portion 105 may move the horizontal moving member 110 along a rail or conveyor 100 and the up and down transfer portion 115 may move the up and down moving member 120 up and down on the horizontal moving member 110.

The rotation portion 135 may be installed at the lower end of the up and down moving member 120 to rotate the mounting portion 127.

While this invention has been described in connection with what is presently considered to be practical exemplary embodiments, it is to be understood that the invention is not limited to the disclosed embodiments. On the contrary, it is intended to cover various modifications and equivalent arrangements included within the spirit and scope of the appended claims.

What is claimed is:

1. A system comprising:
   a dip tank in which fluid is contained, the dip tank having a transparent window from the outside to see the inside;
   a moving device configured to lower a vehicle body into the fluid, to move the vehicle body in the fluid and to raise the vehicle body; and
   a camera installed to detect a form of the vehicle body through the transparent window, wherein the camera is configured to sense a first form of the vehicle body before the vehicle body is immersed in the fluid in the dip tank, to detect an intermediate form of the vehicle body in a state when the vehicle body is moving in the fluid of the dip tank, and to detect a second form of the vehicle body after the vehicle body is removed from the fluid in the dip tank.

2. The system of claim 1, further comprising a processor configured to calculate a variation in the form of the vehicle body according to the first form, the intermediate form and the second form.

3. The system of claim 2, wherein the processor is configured to generate a retest signal depending on the variation in the form of the vehicle body.

4. The system of claim 3, wherein the processor is configured to generate the retest signal when the variation in the form of the vehicle body is determined to be greater than a predetermined value.

5. The system of claim 2, wherein the processor is configured to receive predetermined process conditions and to move the vehicle body to a predetermined speed along a predetermined route according to the process conditions.

6. The system of claim 1, wherein the moving device comprises:
   a mounting portion on which the vehicle body is mounted;
   a horizontal transfer portion for moving the mounting portion in a horizontal direction;
   an up and down transfer portion for moving the mounting portion in the up and down direction; and
   a rotation portion for rotating the mounting portion about a rotation center.

7. The system of claim 6, wherein:
   the horizontal transfer portion comprises a horizontally moving member that moves along a rail;
   the up and down transfer portion comprises a up and down moving member that moves up and down in the horizontal moving member; and
   the rotation portion is disposed on an end portion of the up and down transfer portion in order to rotate the mounting portion.

8. The system of claim 1, wherein the fluid is water, electrodeposition paint, or preprocessing liquid.

9. The system of claim 1, further comprising a circulation device installed to control the flow of the fluid in a fluid space of the dip tank.

10. The system of claim 1, wherein the moving device comprises a conveyor and a lighting device installed inside or outside of the dip tank to illuminate an area where the camera is to photograph.

11. A method of processing a vehicle body, the method comprising:
    putting a vehicle body into a fluid contained in a dip tank that includes a transparent window visible from the outside to the inside;
    moving the vehicle body within the fluid in the dip tank; and
    detecting a form of the vehicle body moving in the dip tank through the transparent window, wherein the detecting comprises:
       sensing a first form of the vehicle body before the vehicle body is immersed in the fluid in the dip tank;
       detecting an intermediate form of the vehicle body in a state when the vehicle body is moving in the fluid of the dip tank; and
       detecting a second form of the vehicle body after the vehicle body is removed from the fluid in the dip tank.

12. The method of claim 11, further comprising exhausting the vehicle body in the fluid to outside the dip tank.

13. The method of claim 12, further comprising calculating a variation of the vehicle body according to the first form, the intermediate form and the second form.

14. The method of claim 13, further comprising generating a reset signal depending on the variation of the form of the vehicle body.

15. The method of claim 14, wherein the reset signal is generated when it is determined that the variation is above a predetermined value.

16. The method of claim 12, further comprising receiving predetermined process conditions, the vehicle body being moved at a set speed according to a set route depending on the process conditions.

17. The method of claim 16, wherein, in the moving step, the vehicle body is moved horizontally, moved up and down, and rotated.

18. The method of claim 12, wherein, the fluid is circulated in the dip tank in a predetermined direction and a predetermined speed.

* * * * *